United States Patent
Lane et al.

(10) Patent No.: US 9,724,513 B2
(45) Date of Patent: Aug. 8, 2017

(54) METHODS TO AVOID FREQUENCY LOCKING IN A MULTI-CHANNEL NEUROSTIMULATION SYSTEM USING PULSE SHIFTING

(75) Inventors: Courtney Lane, Ventura, CA (US); Rafael Carbunaru, Valley Village, CA (US); Kerry Bradley, Glendale, CA (US); David K. L. Peterson, Saugus, CA (US); Andrew DiGiore, Santa Monica, CA (US); Michael Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 2386 days.

(21) Appl. No.: 12/550,213

(22) Filed: Aug. 28, 2009

(65) Prior Publication Data

US 2011/0054567 A1    Mar. 3, 2011

(51) Int. Cl.
*A61N 1/08* (2006.01)
*A61N 1/36* (2006.01)

(52) U.S. Cl.
CPC ......... *A61N 1/36071* (2013.01); *A61N 1/08* (2013.01); *A61N 1/36082* (2013.01); *A61N 1/36171* (2013.01); *A61N 1/36178* (2013.01)

(58) Field of Classification Search
CPC .. A61N 1/36071; A61N 1/36; A61N 1/36125; A61N 1/36014; A61N 1/3606; A61N 1/36185; A61N 1/178; A61N 1/08; A61N 1/336017

USPC .......................................................... 607/2
See application file for complete search history.

(56) References Cited

U.S. PATENT DOCUMENTS

| | | | |
|---|---|---|---|
| 4,398,537 A * | 8/1983 | Holmbo ............ | A61N 1/36071 607/59 |
| 6,516,227 B1 * | 2/2003 | Meadows ............ | A61N 1/0553 607/117 |
| 6,895,280 B2 | 5/2005 | Meadows et al. | |
| 6,993,384 B2 | 1/2006 | Bradley et al. | |
| 7,539,538 B2 | 5/2009 | Parramon et al. | |
| 2003/0139781 A1 | 7/2003 | Bradley et al. | |
| 2005/0267546 A1 | 12/2005 | Parramon et al. | |
| 2007/0225765 A1 * | 9/2007 | King .................. | A61N 1/36164 607/2 |

* cited by examiner

*Primary Examiner* — Michael Kahelin
*Assistant Examiner* — Minh Duc Pham
(74) *Attorney, Agent, or Firm* — Schwegman Lundberg & Woessner, P.A.

(57) ABSTRACT

A method and neurostimulation system for treating a patient are provided. A plurality of pulsed electrical waveforms are respectively delivered within a plurality of timing channels of the neurostimulation system, thereby treating the patient. Sets of stimulation pulses within the pulsed electrical waveforms that will potentially overlap temporally are predicted. Stimulation pulses in the respective pulsed electrical waveforms are temporally shifted in a manner that prevents overlap of the potentially overlapping pulse sets while preventing frequency locking between the timing channels.

14 Claims, 14 Drawing Sheets

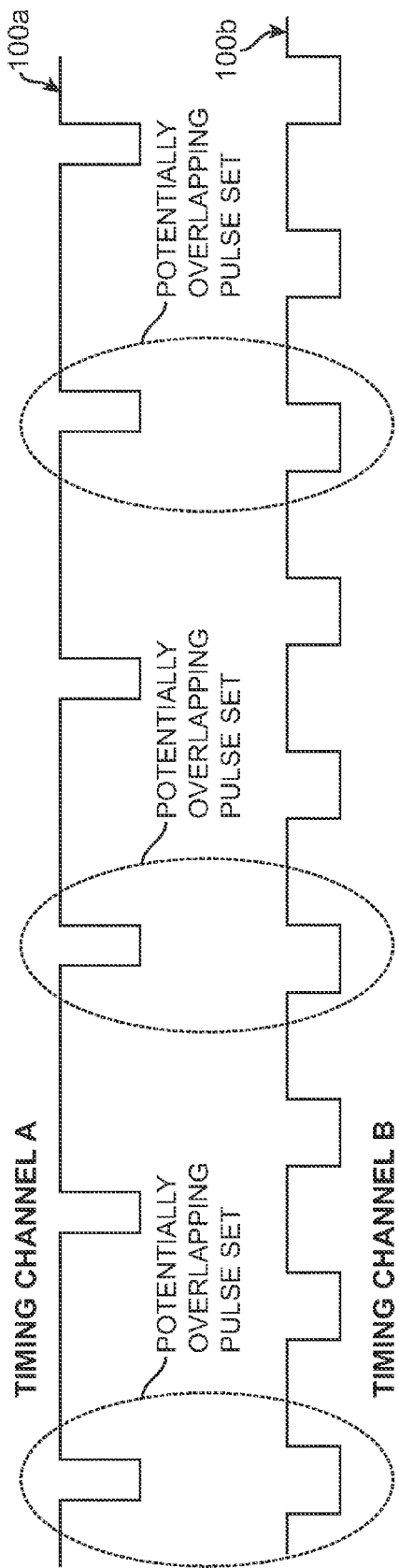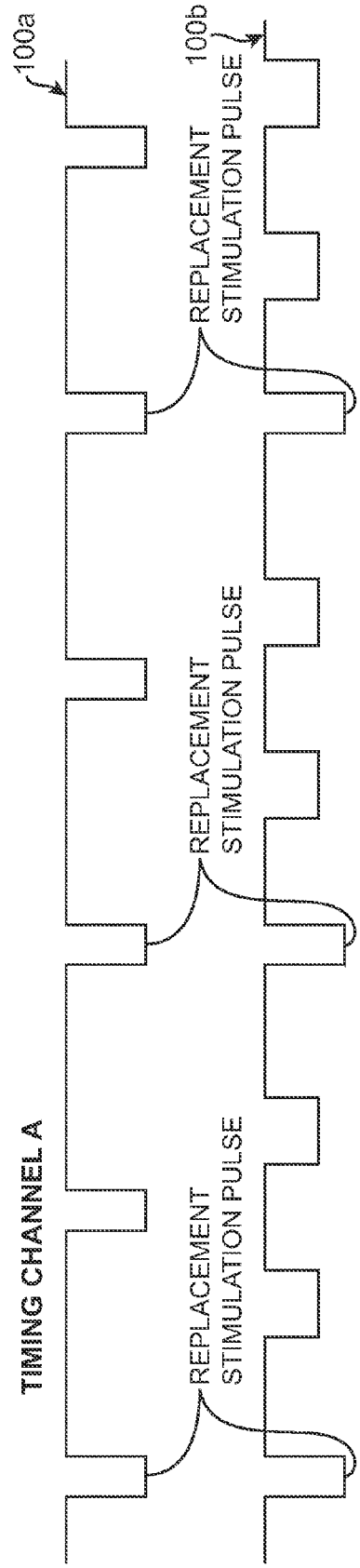

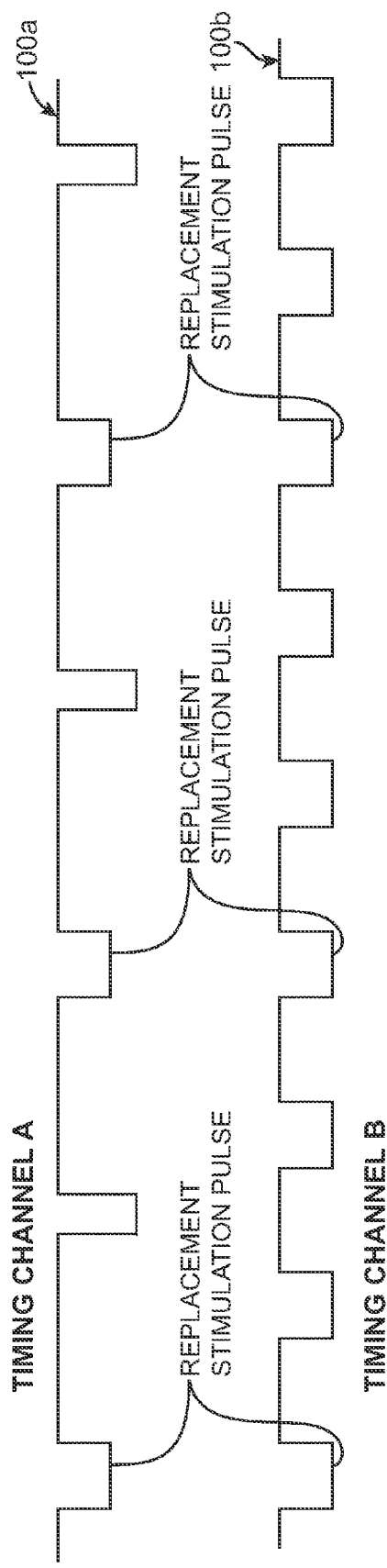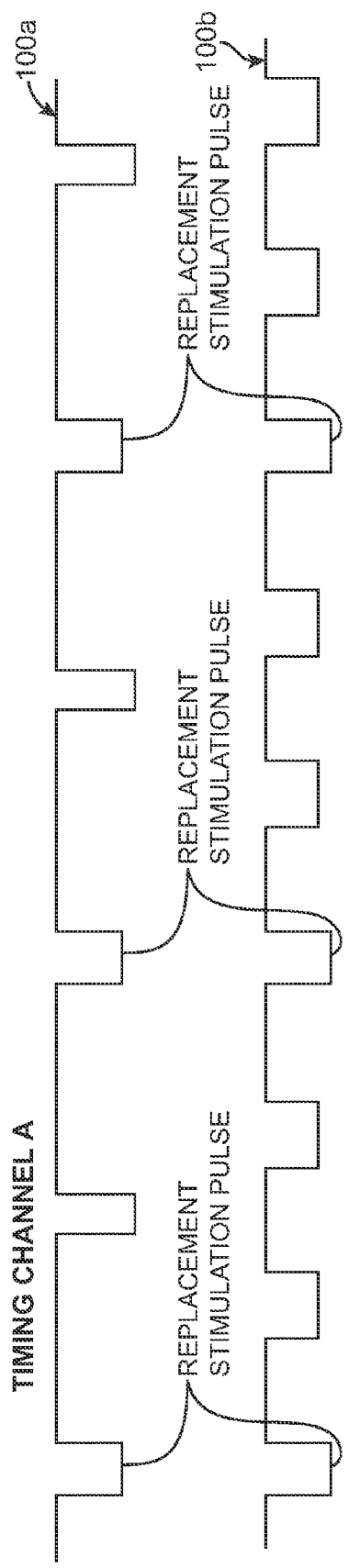

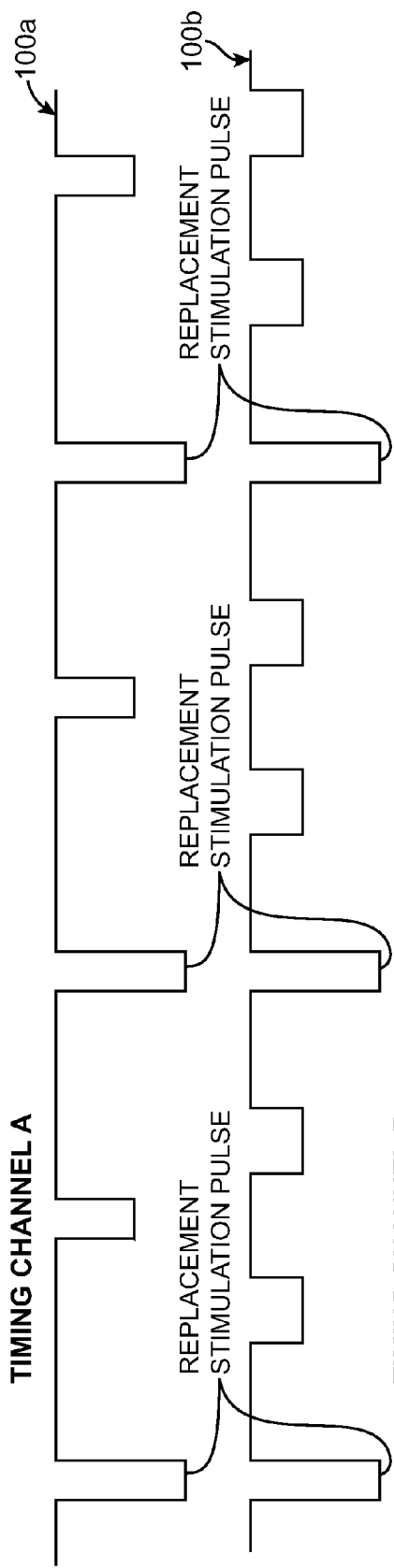
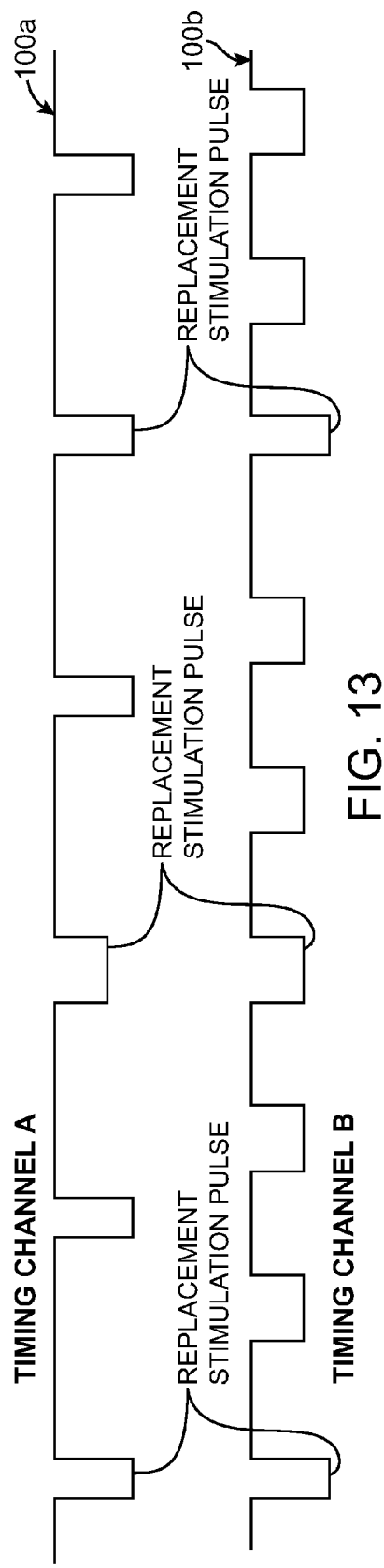
FIG. 12
FIG. 13

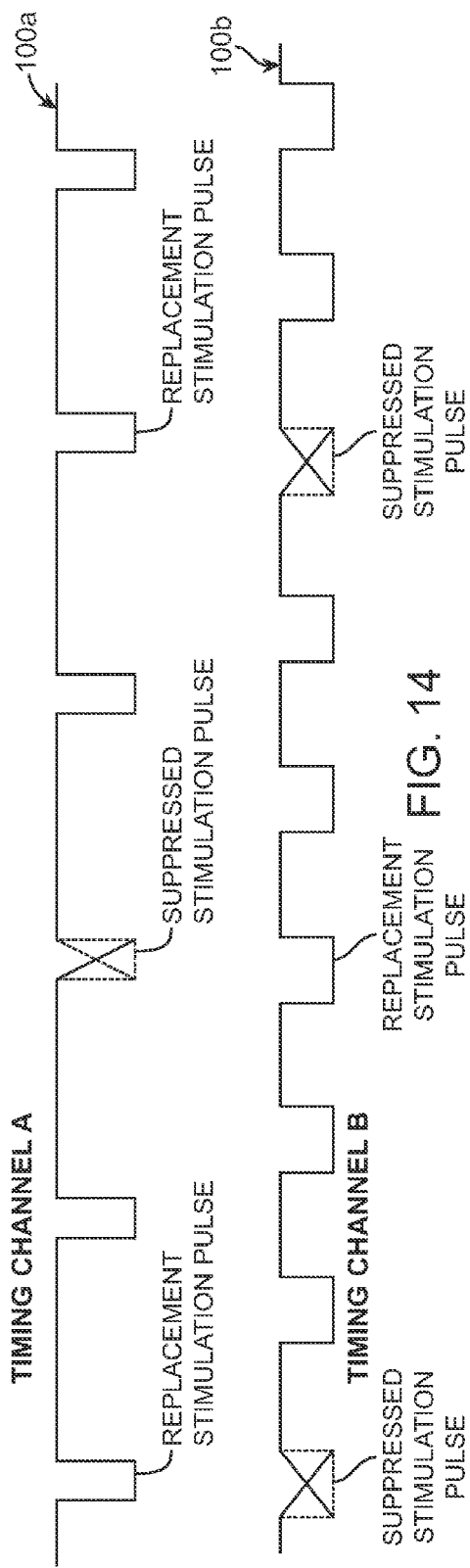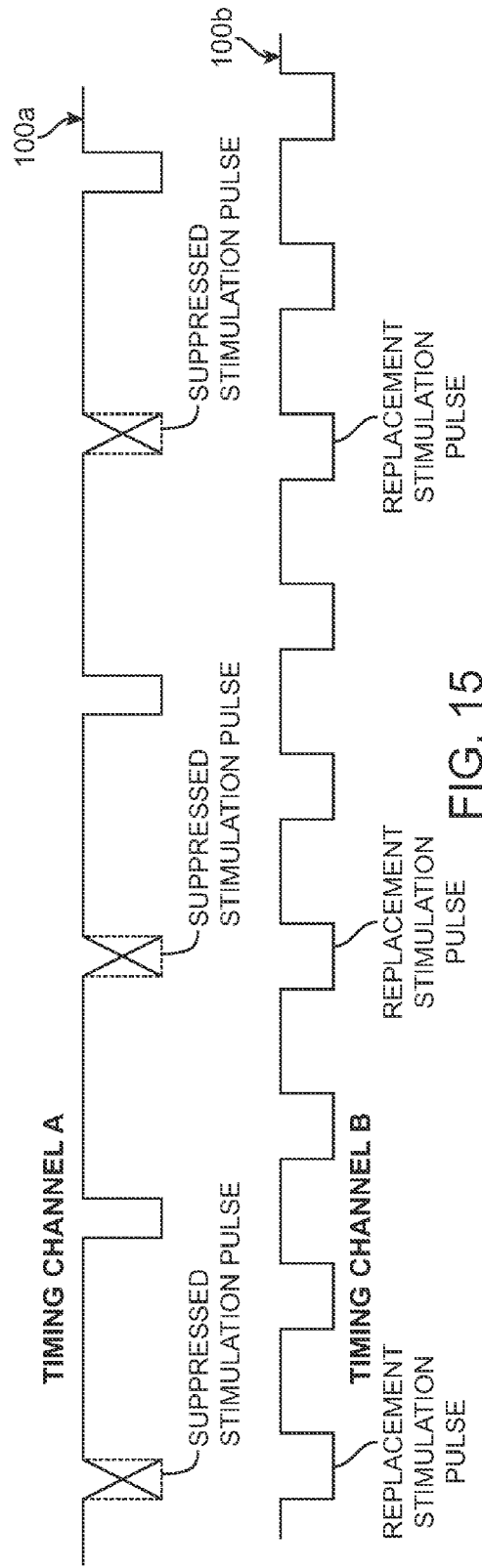

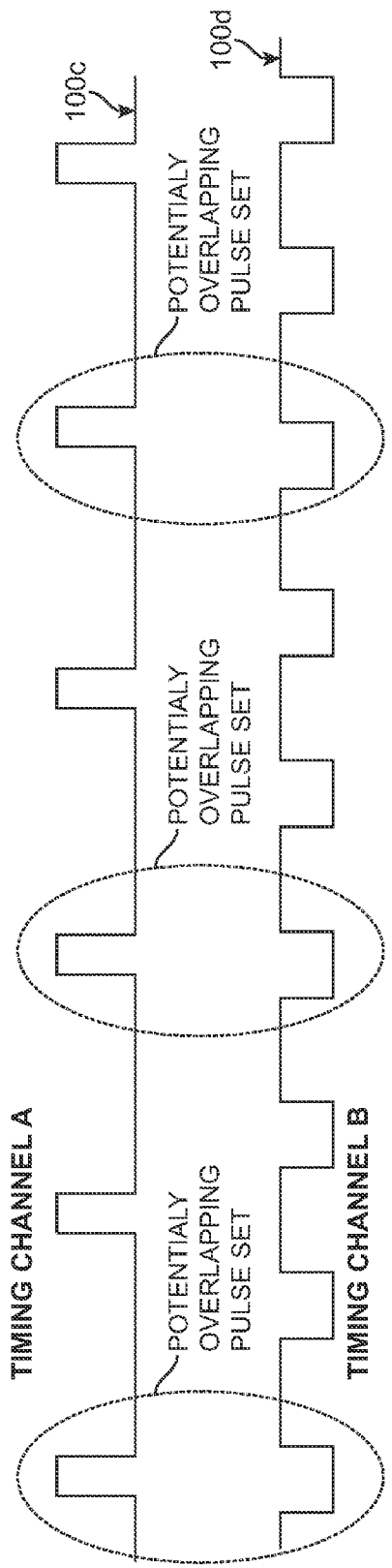
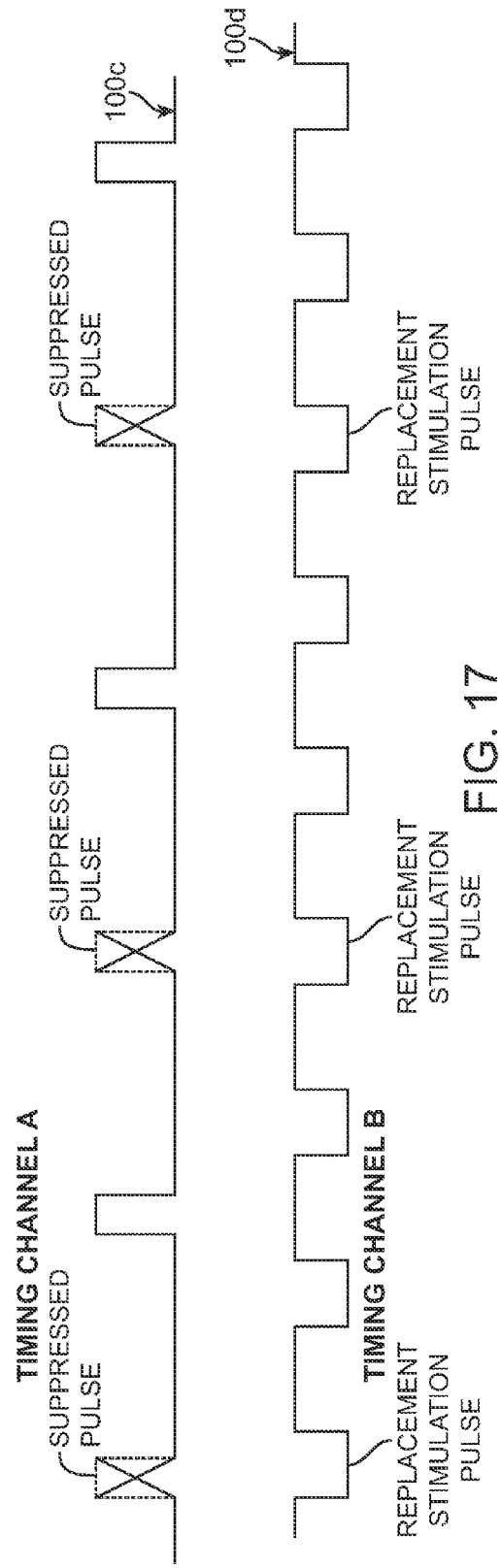

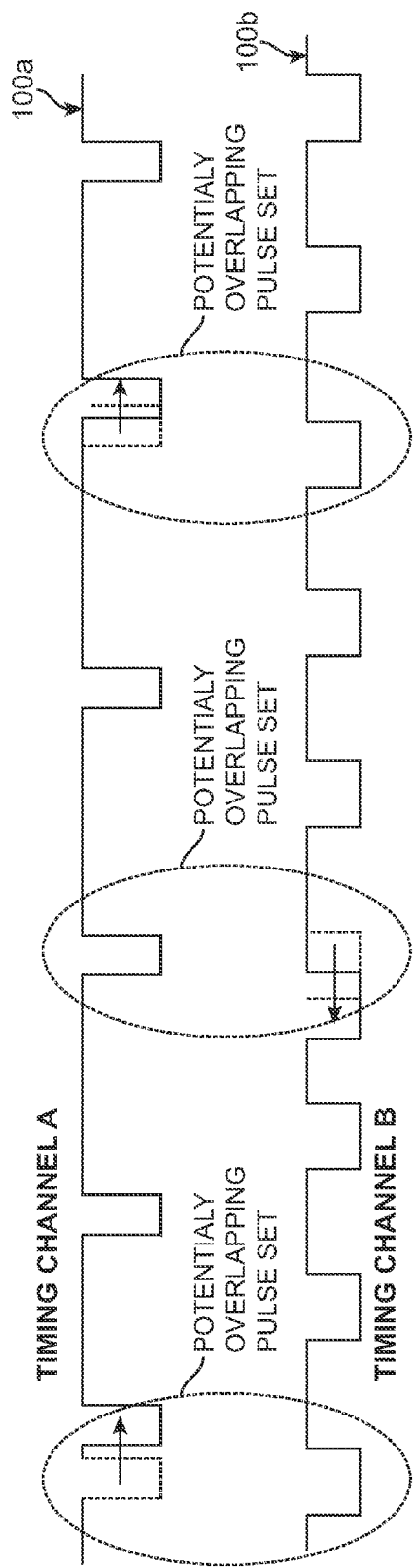
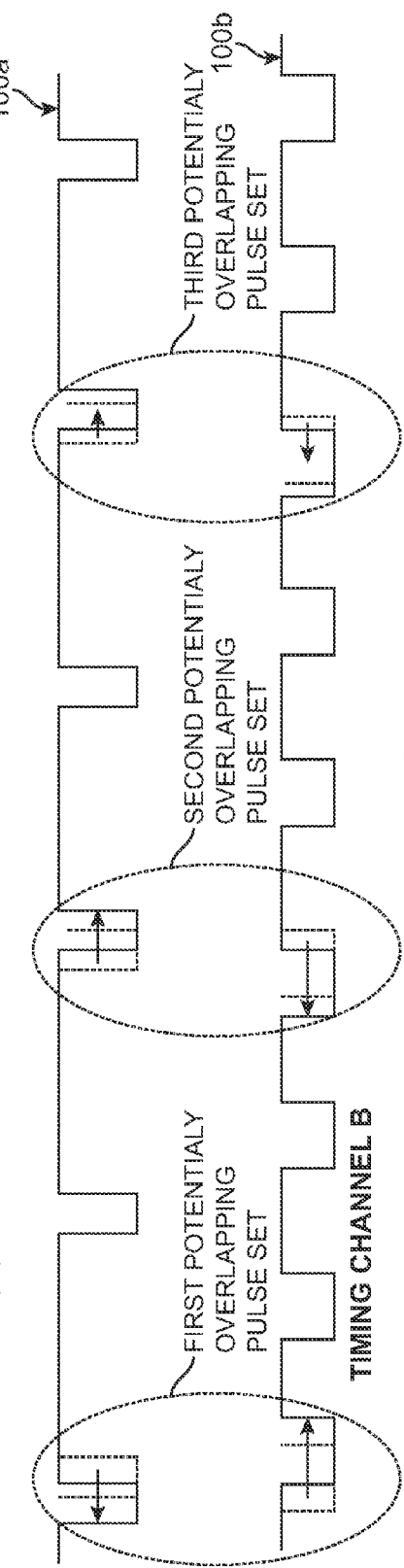

METHODS TO AVOID FREQUENCY LOCKING IN A MULTI-CHANNEL NEUROSTIMULATION SYSTEM USING PULSE SHIFTING

FIELD OF THE INVENTION

The present invention relates to tissue stimulation systems, and more particularly, to a system and method for eliminating or reducing frequency locking in multi-channel neurostimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an pulsed electrical waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, duration, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. However, the number of electrodes available combined with the ability to generate a variety of complex stimulation pulses, presents a vast selection of stimulation parameter sets to the clinician or patient.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

Often, multiple timing channels are used when applying electrical stimulation to target different tissue regions in a patient. For example, in the context of SCS, the patient may simultaneously experience pain in different regions (such as the lower back, left arm, and right leg) that would require the electrical stimulation of different spinal cord tissue regions. In the context of DBS, a multitude of brain structures may need to be electrically stimulated in order to simultaneously treat ailments associated with these brain structures. Each timing channel identifies the combination of electrodes used to deliver electrical pulses to the targeted tissue, as well as the characteristics of the current (pulse amplitude, pulse duration, pulse frequency, etc.) flowing through the electrodes.

The use of multiple timing channels can often lead to problems with the electrical stimulation systems due to the potential of an overlap in pulses between two or more timing channels. Overlapping of pulses using a common electrode can make neurostimulation systems ineffective or even harmful. Current neurostimulation systems employing multiple timing channels use a method known as the "token" method to prevent overlap of pulses. This method allows an electrical pulse to be transmitted in the timing channel with the "token," while the other timing channels wait their turn. Then, the "token" is passed to the next timing channel. However, if the frequencies of the channels overlap, such that they need the "token" at the same time, transmission of an electrical pulse within the second channel must wait until the end of the transmission of the electrical pulse in the first timing channel. One possible result is that the frequency of the electrical pulses transmitted in the second timing channel gets "locked" to (i.e. matches) the frequency of the electrical pulses transmitted in the first timing channel; alternatively, one can get galloping or clumping of electrical pulses. Therefore, when the occurrence of stimulation pulses is pushed out in time, stimulation therapy becomes ineffective or even harmful for tissue regions, such as brain structures to be stimulated in DBS applications, that require stimulation at specific, regular frequencies.

The "token" method may best be understood with reference to FIG. 1. As there shown, a first pulsed electrical waveform 5a having a first frequency is transmitted within timing channel A, and a second pulsed electrical waveform 5b having a second frequency is desired to be transmitted within timing channel B. Because timing channel A has the "token," the pulses of the second pulsed electrical waveform 5b that are to be transmitted in timing channel B must be "bumped" each time they overlap with the pulses of the first pulsed electrical waveform 5a. As can be seen in the bumped pulsed electrical waveform 5c, when a pulse is bumped (shown by the horizontal arrows), the next pulse relies on the new (bumped) pulse for timing. Thus, the next pulse is "double bumped": once when the previous pulse is bumped and a second time when it overlaps a pulse of the pulsed electrical waveform 5a transmitted in the timing channel A. As a result, the frequency of the pulses in the second pulsed electrical waveform 5b is forced (i.e., locked) into the frequency for the first pulsed electrical waveform 5a, resulting in a pulsed electrical waveform 5d that has a frequency twice as small as the desired frequency.

There, thus, remains a need to provide an improved method for preventing or minimizing frequency locking within multi-channel neurostimulation systems.

SUMMARY OF THE INVENTION

In accordance with a first aspect of the present inventions, a method for treating a patient using a multi-channel neurostimulation system is provided. The method comprises delivering a plurality of pulsed electrical waveforms respectively within a plurality of timing channels of the neurostimulation system, thereby treating the patient.

The method comprises delivering a plurality of pulsed electrical waveforms respectively within a plurality of timing channels of the neurostimulation system, thereby treating the patient. In one method, the pulsed electrical waveforms are delivered via a common electrode and have different pulse frequencies. The pulsed electrical waveforms may, e.g., be defined in response to a user input. The method further comprises predicting sets of stimulation pulses within the electrical waveforms that will potentially overlap temporally. In one method, the stimulation pulses of each of the potentially overlapping pulse sets have the same polarity. The method further comprises temporally shifting stimulation pulses in the respective pulsed electrical waveforms in a manner that prevents overlap of the potentially overlapping pulse sets while preventing frequency locking between the timing channels. An optional method further comprises predicting a charge recovery pulse and a stimulation pulse within the electrical waveforms that will potentially overlap temporally, and dropping or temporally shifting at least a portion of the charge recovery pulse, thereby preventing temporal overlap between the charge recovery pulse and the stimulation pulse of the respective electrical waveforms. In one embodiment, each replacement stimulation pulse is delivered within all of the respective timing channels.

In one method, the temporal shifting of the stimulation pulses in the respective pulsed electrical waveforms comprises alternately shifting one of the stimulation pulses of each potentially overlapping pulse set between the timing channels. In another method, the temporal shifting of stimulation pulses in the respective pulsed electrical waveforms comprises temporally shifting one of the stimulation pulses of each potentially overlapping pulse set forward, and temporally shifting another of the stimulation pulses of each potentially overlapping pulse set backward. In still another method, the temporal shifting of the stimulation pulses in the respective pulsed electrical waveforms comprises determining which pulse of each potentially overlapping pulse set would need to be shifted the least to prevent overlapping of the stimulation pulses within the respective potentially overlapping pulse set, and temporally shifting the determined pulse of each potentially overlapping pulse set. In yet another method, the temporal shifting of the stimulation pulses in the respective pulsed electrical waveforms comprises determining sets of stimulation pulses within the pulsed electrical waveforms that will not potentially overlap temporally, and temporally shifting at least one pulse in each of the non-overlapping pulse sets. In yet another method, the temporal shifting of the stimulation pulses in the respective pulsed electrical waveforms comprises temporally shifting at least one pulse in each potentially overlapping pulse set a random amount. In this case, the method may further comprise determining the random amount by multiplying a nominal pulse shift by a randomization variable. This method may further comprise limiting the random amount that differs from the nominal pulse shift.

In accordance with a second aspect of the present inventions, a multi-channel neurostimulation system is provided. The neurostimulation system comprises a plurality of electrical terminals configured for being respectively coupled to a plurality of electrodes, and analog output circuitry configured for delivering a plurality of pulsed electrical waveforms respectively within a plurality of timing channels to the electrical terminals. In one embodiment, the stimulation pulses of each of the potentially overlapping pulse sets have the same polarity. In another embodiment, the analog output circuitry is configured for delivering the pulsed electrical waveforms via a common electrode. In another embodiment, the pulsed electrical waveforms have different pulse frequencies.

The neurostimulation system comprises control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels. In an optional embodiment, the control circuitry is further configured for predicting a charge recovery pulse and a stimulation pulse within the electrical waveforms that will potentially overlap temporally, and dropping or temporally shifting at least a portion of the charge recovery pulse, thereby preventing temporal overlap between the charge recovery pulse and the stimulation pulse of the respective electrical waveforms.

In one embodiment, the control circuitry is configured for shifting stimulation pulses in the respective pulsed electrical waveforms by alternately shifting one of the stimulation pulses of each potentially overlapping pulse set between the timing channels. In another embodiment, the control circuitry is configured for temporally shifting stimulation pulses in the respective pulsed electrical by temporally shifting one of the stimulation pulses of each potentially overlapping pulse set forward, and temporally shifting another of the stimulation pulses of each potentially overlapping pulse set backward. In still another embodiment, the control circuitry is configured for temporally shifting stimulation pulses in the respective pulsed electrical waveforms by determining which pulse of each potentially overlapping pulse set would need to be shifted the least to prevent overlapping of the stimulation pulses within the respective potentially overlapping pulse set, and temporally shifting the determined pulse of each potentially overlapping pulse set. In yet another embodiment, the control circuitry is configured for temporally shifting stimulation pulses in the respective pulsed electrical waveforms by determining sets of stimulation pulses within the pulsed electrical waveforms that will not potentially overlap temporally, and temporally shifting at least one pulse in each of the non-overlapping pulse sets. In yet another embodiment, the control circuitry is configured for temporally shifting stimulation pulses in the respective pulsed electrical waveforms by temporally shifting at least one pulse in each potentially overlapping pulse set a random amount. In this case, the control circuitry may be configured for determining the random amount by multiplying a nominal pulse shift by a randomization variable. The control circuitry may also be further configured for limiting the random amount that differs from the nominal pulse shift.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a timing diagram of two pulsed electrical waveforms delivered within two respective timing channels of the IPG of FIG. 3, wherein pulses of the respective electrical waveforms temporally overlap with each other;

FIG. 9 is a timing diagram of two pulsed electrical waveforms delivered within two respective timing channels of the IPG of FIG. 3, wherein a first technique is used to prevent temporal overlap between the pulses of the respective electrical waveforms;

FIG. 10 is a timing diagram of two pulsed electrical waveforms delivered within two respective timing channels of the IPG of FIG. 3, wherein a second technique is used to prevent temporal overlap between the pulses of the respective electrical waveforms;

FIG. 11 is a timing diagram of two pulsed electrical waveforms delivered within two respective timing channels of the IPG of FIG. 3, wherein a third technique is used to prevent temporal overlap between the pulses of the respective electrical waveforms;

FIG. 12 is a timing diagram of two pulsed electrical waveforms delivered within two respective timing channels of the IPG of FIG. 3, wherein a fourth technique is used to prevent temporal overlap between the pulses of the respective electrical waveforms;

FIG. 13 is a timing diagram of two pulsed electrical waveforms delivered within two respective timing channels of the IPG of FIG. 3, wherein a fifth technique is used to prevent temporal overlap between the pulses of the respective electrical waveforms;

FIG. 14 is a timing diagram of two pulsed electrical waveforms delivered within two respective timing channels of the IPG of FIG. 3, wherein a sixth technique is used to prevent temporal overlap between the pulses of the respective electrical waveforms;

FIG. 15 is a timing diagram of two pulsed electrical waveforms delivered within two respective timing channels of the IPG of FIG. 3, wherein a seventh technique is used to prevent temporal overlap between the pulses of the respective electrical waveforms;

FIG. 16 is a timing diagram of two pulsed electrical waveforms delivered within two respective timing channels of the IPG of FIG. 3, wherein pulses of the respective electrical waveforms temporally overlap with each other;

FIG. 17 is a timing diagram of two pulsed electrical waveforms delivered within two respective timing channels of the IPG of FIG. 3, wherein an eighth technique is used to prevent temporal overlap between the pulses of the respective electrical waveforms;

FIG. 18 is a timing diagram of two pulsed electrical waveforms delivered within two respective timing channels of the IPG of FIG. 3, wherein a ninth technique is used to prevent temporal overlap between the pulses of the respective electrical waveforms;

FIG. 19 is a timing diagram of two pulsed electrical waveforms delivered within two respective timing channels of the IPG of FIG. 3, wherein a tenth technique is used to prevent temporal overlap between the pulses of the respective electrical waveforms;

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
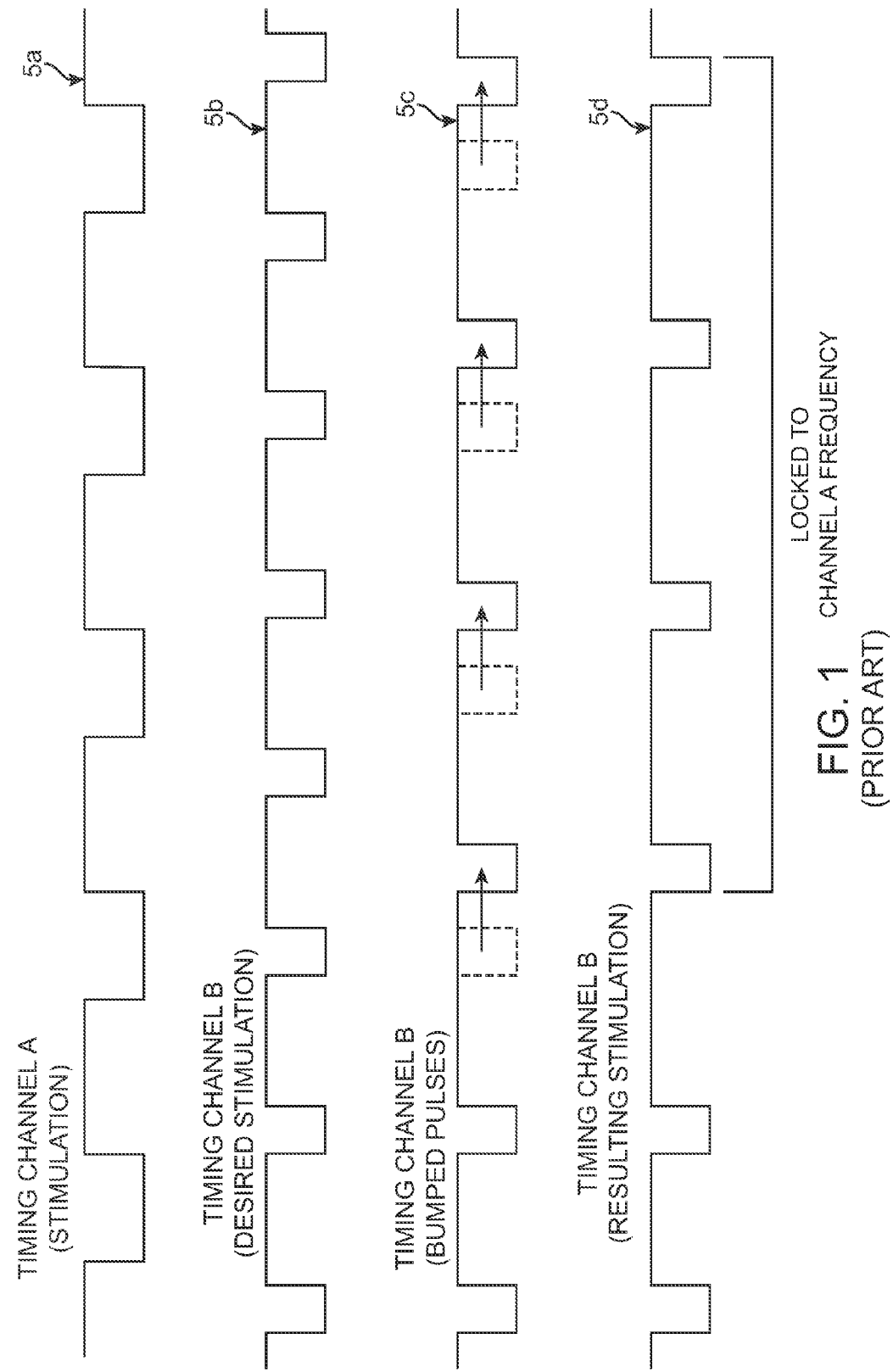
FIG. 1 is timing diagram illustrating a prior art technique for preventing the overlap between pulses of pulsed electrical waveforms programmed in multiple timing channels.
Figure 2:
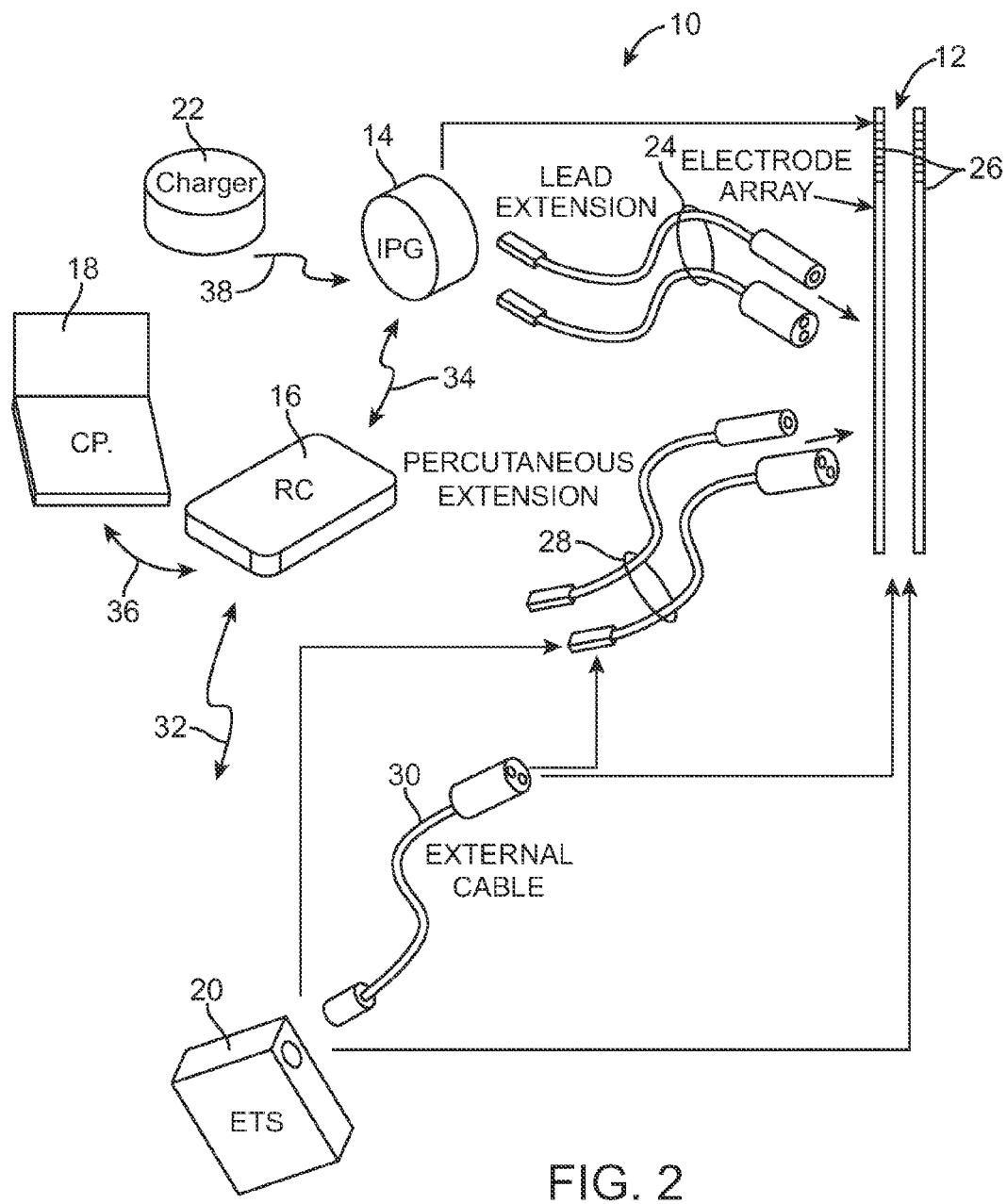
FIG. 2 is a plan view of an embodiment of a deep brain stimulation (DBS) system arranged in accordance with the present inventions.

Turning first to FIG. 2, an exemplary DBS neurostimulation system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 may be arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 3:
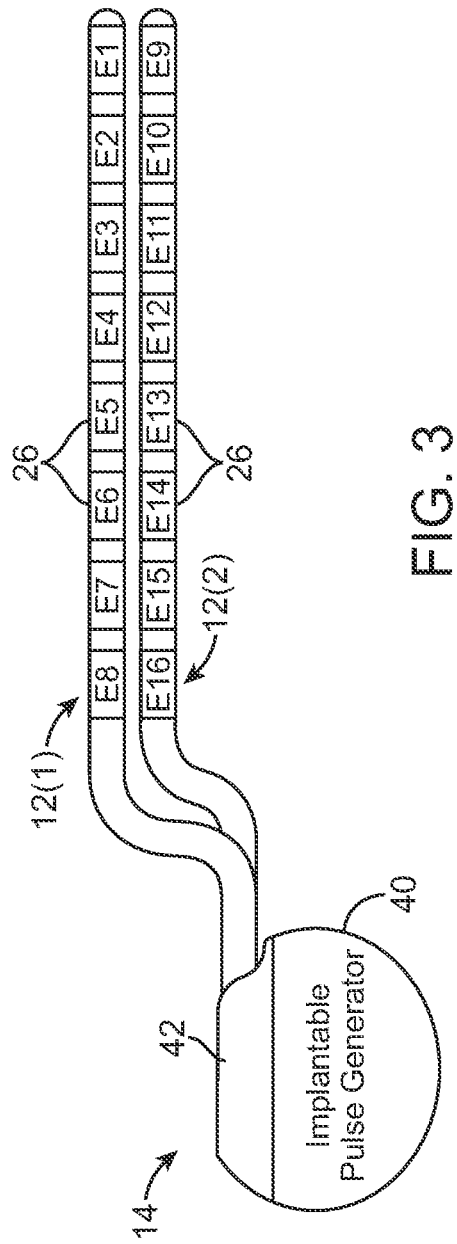
FIG. 3 is a profile view of an implantable pulse generator (IPG) and percutaneous leads used in the DBS system of FIG. 2.

Referring now to FIG. 3, the features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Figure 4:
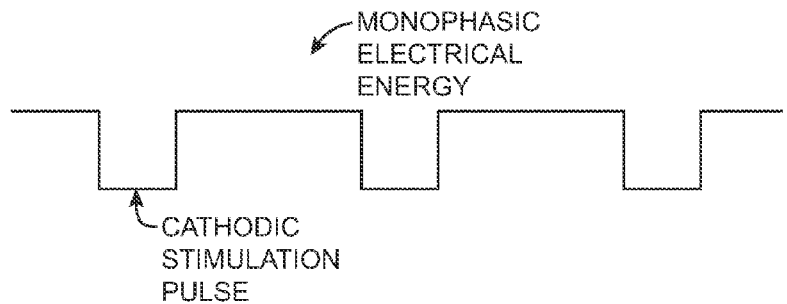
FIG. 4 is a plot of monophasic cathodic electrical stimulation energy.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(1) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode The stimulation energy may be delivered between a specified group of electrodes as monophasic electrical energy or multiphasic electrical energy. As illustrated in FIG. 4, monophasic electrical energy includes a series of pulses that are either all negative (cathodic), or alternatively all positive (anodic). Multiphasic electrical energy includes a series of pulses that alternate between positive and negative.

Figure 5A:
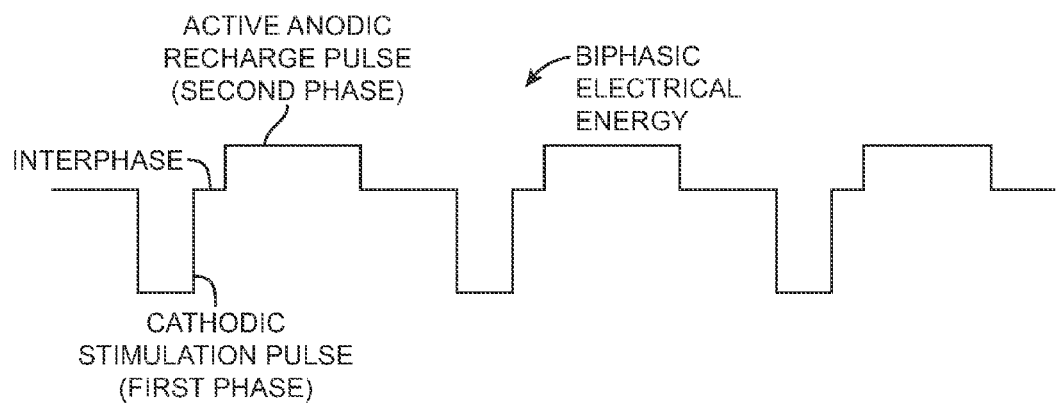
FIG. 5*a* is a plot of biphasic electrical stimulation energy having a cathodic stimulation pulse and an active charge recovery pulse.
Figure 5B:
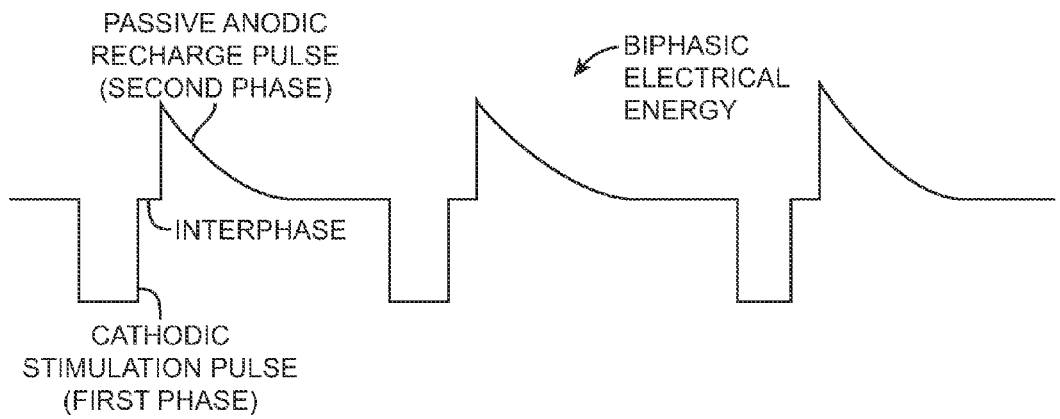
FIG. 5*b* is a plot of biphasic electrical stimulation energy having a cathodic stimulation pulse and a passive charge recovery pulse.

For example, as illustrated in FIGS. 5a and 5b, multiphasic electrical energy may include a series of biphasic pulses, with each biphasic pulse including a cathodic (negative) stimulation pulse (during a first phase) and an anodic (positive) charge recovery pulse (during a second phase) that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, and a passive charge recovery pulse, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

Figure 6:
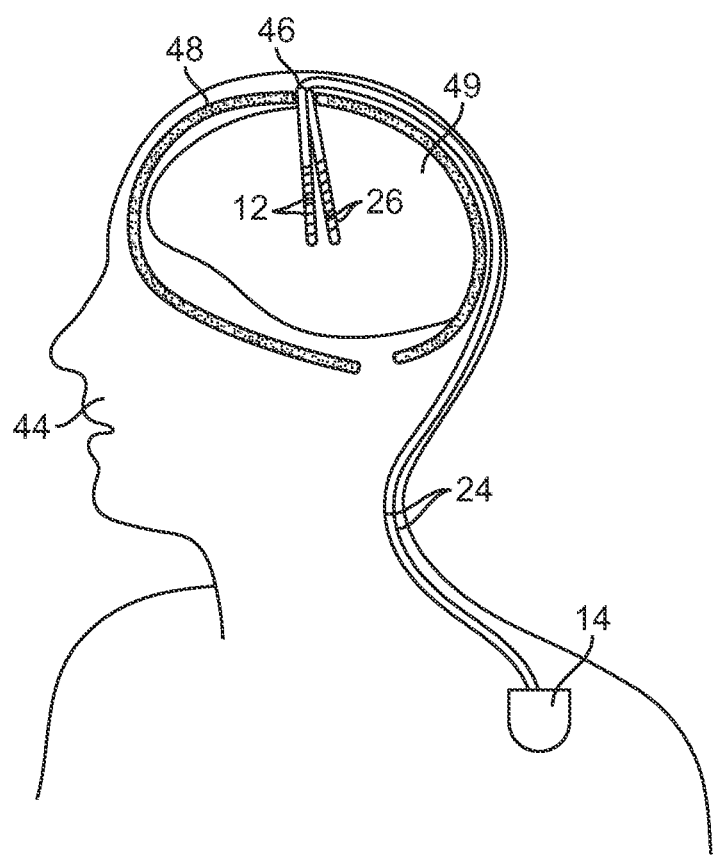
FIG. 6 is a plan view of the DBS system of FIG. 2 in use with a patient.

As shown in FIG. 6, the stimulation leads 12 are introduced through a burr hole 46 formed in the cranium 48 of a patient 44, and introduced into the parenchyma of the brain 49 of the patient 44 in a conventional manner, such that the electrodes 26 are adjacent a target tissue region whose electrical activity is the source of the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the stimulation leads 12 exit the burr hole 46, the IPG 14 is generally implanted in a surgically-made pocket either in the abdomen or above the buttocks. The IPG 14 may, of course, also be implanted in other locations of the patient's body. The lead extension(s) 24 facilitates locating the IPG 14 away from the exit point of the electrode leads 12.

Figure 7:
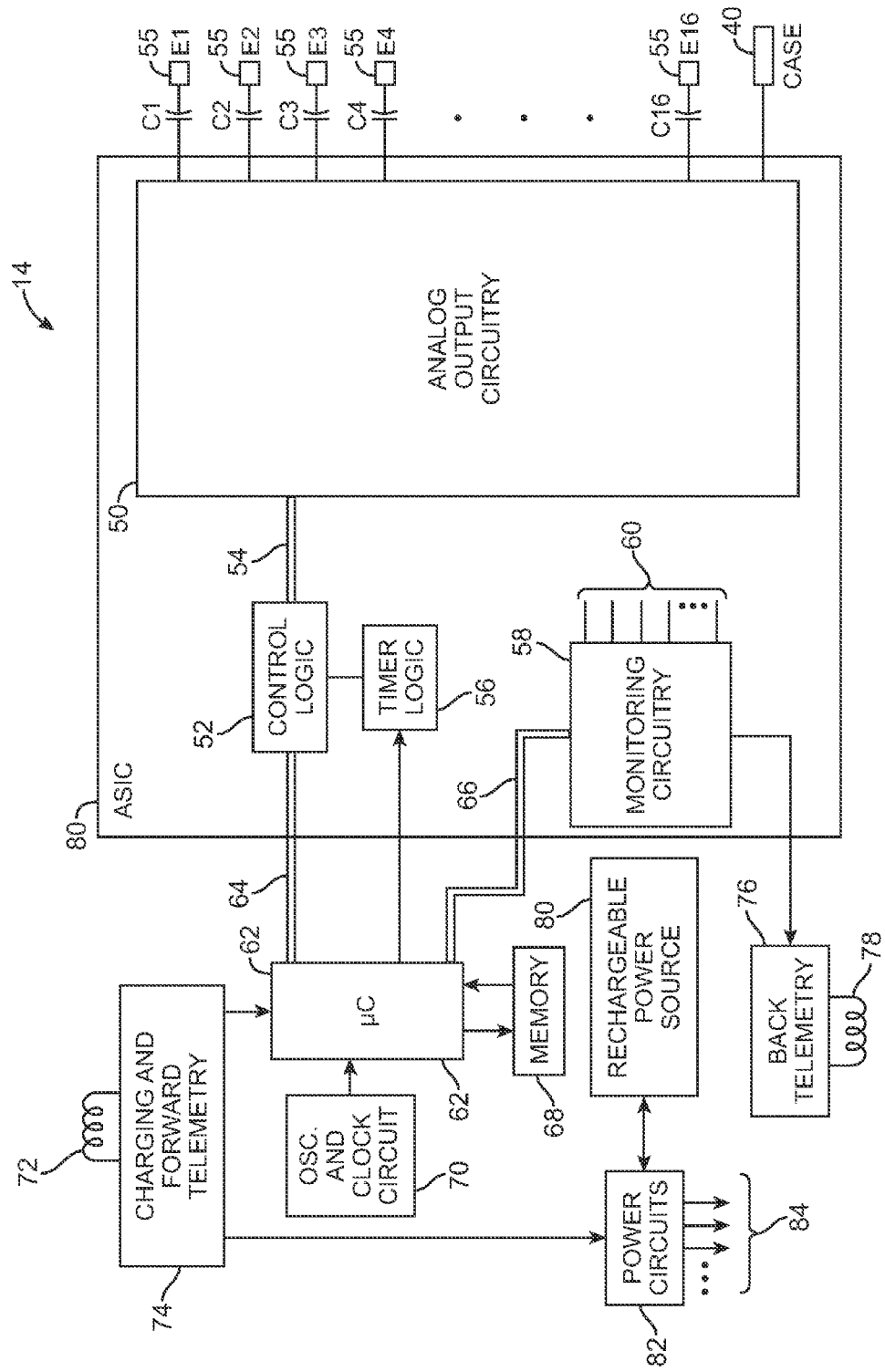
FIG. 7 is a block diagram of the internal components of the IPG of FIG. 3.

Turning next to FIG. 7, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 μs. The stimulation energy generated by the stimulation output circuitry 50 is output via capacitors C1-C16 to electrical terminals 55 corresponding to the electrodes 26. The analog output circuitry 50 may either comprise independently controlled current sources for providing stimulation pulses of a specified and known amperage to or from the electrodes 26, or independently controlled voltage sources for providing stimulation pulses of a specified and known voltage at the electrodes 26.

Any of the N electrodes may be assigned to up to k possible groups or "channels." In one embodiment, k may equal four. The channel identifies which electrodes are selected to synchronously source or sink current to create an electric field in the tissue to be stimulated. Amplitudes and polarities of electrodes on a channel may vary, e.g., as controlled by the RC 16. External programming software in the CP 18 is typically used to set stimulation parameters including electrode polarity, amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 pulses per second (pps). Other programmable features can include slow start/end ramping, burst stimulation cycling (on for X time, off for Y time), interphase, and open or closed loop sensing modes.

The operation of this analog output circuitry 50, including alternative embodiments of suitable output circuitry for performing the same function of generating stimulation pulses of a prescribed amplitude and duration, is described more fully in U.S. Pat. Nos. 6,516,227 and 6,993,384, which are expressly incorporated herein by reference.

The IPG 14 further comprises monitoring circuitry 58 for monitoring the status of various nodes or other points 60 throughout the IPG 14, e.g., power supply voltages, temperature, battery voltage, and the like. The IPG 14 further comprises processing circuitry in the form of a microcontroller (μC) 62 that controls the control logic over data bus 64, and obtains status data from the monitoring circuitry 58 via data bus 66. The IPG 14 additionally controls the timer logic 56. The IPG 14 further comprises memory 68 and oscillator and clock circuitry 70 coupled to the microcontroller 62. The microcontroller 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the microcontroller 62 generates the necessary control and status signals, which allow the microcontroller 62 to control the operation of the IPG 14 in accordance with a selected operating program and stimulation parameters. In controlling the operation of the IPG 14, the microcontroller 62 is able to individually generate a train of stimulus pulses at the electrodes 26 using the analog output circuitry 60, in combination with the control logic 52 and timer logic 56, thereby allowing each electrode 26 to be paired or grouped with other electrodes 26, including the monopolar case electrode. In accordance with stimulation parameters stored within the memory 68, the microcontroller 62 may control the polarity, amplitude, rate, pulse duration and channel through which the current stimulus pulses are provided. The microcontroller 62 also facilitates the storage of electrical parameter data (or other parameter data) measured by the monitoring circuitry 58 within memory 68, and also provides any computational capability needed to analyze the raw electrical parameter data obtained from the monitoring circuitry 58 and compute numerical values from such raw electrical parameter data.

Significantly, as will be described in further detail below, the microcontroller 62 uses a set of rules to prevent overlap of pulses between multiple timing channels. Alternatively, functions such as the management of stimulation pulses and timing information may be performed in a digital state machine, with the microcontroller 62 having a supervisory role to manage information flow, e.g., sending stimulation parameters to the analog circuitry and/or converting sampled analog data into a digital form, and then post-processing the digital data for storage or transmission to the RC 16.

The IPG 14 further comprises an alternating current (AC) receiving coil 72 for receiving programming data (e.g., the operating program and/or stimulation parameters) from the RC 16 (shown in FIG. 2) in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 14.

The IPG 14 further comprises back telemetry circuitry 76 and an alternating current (AC) transmission coil 78 for sending informational data sensed through the monitoring circuitry 58 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 68 to be downloaded from the IPG 14 to the RC 16, which information can be used to track the physical activity of the patient.

The IPG 14 further comprises a rechargeable power source 80 and power circuits 82 for providing the operating power to the IPG 14. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 14. The rechargeable power source 80 is recharged using rectified AC power (or DC power converted from AC power through other means, e.g., efficient AC-to-DC converter circuits, also known as "inverter circuits") received by the AC receiving coil 72. To recharge the power source 80, an external charger (not shown), which generates the AC magnetic field, is placed against, or otherwise adjacent, to the patient's skin over the implanted IPG 14. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

It should be noted that the diagram of FIG. 7 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the DBS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the IPG 14 may be programmed by the CP 18 (or alternatively the RC 16) to operate over multiple timing channels. The IPG 14 may prevent overlap between the electrical pulses generated in the respective timing channels, and to do so without frequency locking occurring between the timing channels. While the techniques described herein for preventing overlapping of electrical pulses and frequency locking between timing channels lend themselves well when the electrode combinations assigned to the respective timing channels have one or more common electrodes, these techniques may be useful even if the electrode combinations assigned to the respective timing channels are completely different from each other. These techniques will now be described.

Referring first to FIG. 8, two timing channels (Channel A and Channel B) of the IPG 14 may be programmed by the CP 18 (or alternatively, the RC 16) with two pulsed electrical waveforms 100a, 100b, respectively, which when delivered by the analog output circuitry 50 of the IPG 14, will provide treatment to the patient in which the IPG 14 has been implanted. The electrode combinations assigned to the respective timing channels will typically be those that result in the treatment of two different regions. As briefly discussed above, each timing channel identifies the electrodes that are selected to synchronously source or sink current to create an electrical field in the tissue to be stimulated, and that the amplitude and polarities of electrodes assigned to each timing channel may vary. Notably, more than one pulsed electrical waveform can be delivered within any particular timing channel, such as those exemplified in U.S. Pat. No. 6,895,280, which has been previously incorporated herein by reference. For purposes of brevity and clarity, however, only one pulsed electrical waveform is shown for each timing channel. Furthermore, although the pulsed electrical waveforms illustrated in FIG. 8 are monophasic in nature, the pulsed electrical waveforms delivered during a timing channel can be multiphasic in nature, as described in further detail below.

As seen in FIG. 8, without modification, certain sets of respective stimulation pulses of the electrical waveforms 100*a*, 100*b* will temporally overlap each other (either partially or completely). However, the microcontroller 62 of the IPG 14 may predict the sets of stimulation pulses that will potentially overlap each other temporally prior to their delivery within the respective timing channels, and replace each of these potentially overlapping pulse sets with a stimulation pulse, such that each replacement stimulation pulse is delivered within at least one of the respective timing channels (and thus, delivered to the both electrode combinations assigned to the timing channels in the case where the electrode combinations are the same for both timing channels), thereby preventing temporal overlap between the stimulation pulses of the respective pulsed electrical waveforms 100*a*, 100*b* while preventing frequency locking between the timing channels. If delivered in both timing channels, the replacement stimulation pulse will preferably be simultaneously delivered within the timing channels. If the potentially overlapping stimulation pulses that are replaced are displaced from each other in time, then the replacement stimulation pulse may be slightly displaced or offset in time from the potentially overlapping pulses that they replace.

In one embodiment, the IPG 14 may determine the relative amplitude and/or duration (width) of the pulses within each potentially overlapping pulse set, and select the single replacement stimulation pulse for each potentially overlapping pulse set based on the determined relative amplitude and/or pulse duration, with each replacement stimulation pulse being delivered within both timing channels. For example, as shown in FIG. 9, for each potentially overlapping pulse set, the IPG 14 selects the stimulation pulse having the largest amplitude as the replacement stimulation pulse. In this manner, any difference between the amount current delivered to the electrode combinations by a set of non-overlapping stimulation pulses of the respective pulsed electrical waveforms 100*a*, 100*b* and the amount of current delivered to the electrode combinations by the replacement stimulation pulse (which will have to be distributed amongst two combinations of electrodes) is minimized. Alternatively, the pulse with the largest duration may be selected as the replacement stimulation pulse, as shown in FIG. 10.

In another embodiment, the IPG 14 may define each of the replacement stimulation pulses as a function of the stimulation pulses within the respective potentially overlapping pulse set that is replaced, with each replacement stimulation pulse being delivered within both timing channels. For example, as shown in FIG. 11, for each potentially overlapping pulse set, the IPG 14 averages the amplitudes and the pulse widths of the respective stimulation pulses within the pulse set and uses this average as the amplitude and pulsewidth of the replacement stimulation pulse. Alternatively, the IPG 14 may average only the amplitudes or only the durations of the respective pulses within the pulse set and use this average as the respective amplitude or duration of the replacement stimulation pulse.

As another example shown in FIG. 12, for each potentially overlapping pulse set, the IPG 14 sums the amplitudes of the respective stimulation pulses within the pulse set and uses this sum as the amplitude of the replacement stimulation pulse. By summing the pulses in each potentially overlapping pulse set, a sufficient amount of electrical current delivered in each timing channel will be ensured, so that the respective tissue regions of the patient will be adequately stimulated. The IPG 14 may limit the amplitude of each replacement stimulation pulse (e.g., 20 mA) to prevent over-stimulation of either tissue regions, and in particular, the tissue region associated with the timing channel having the lower amplitude pulses.

In still another embodiment, the IPG 14 may alternately select the stimulation pulse of the respective pulsed electrical waveforms 100*a*, 100*b* as the replacement stimulation pulse for each of the potentially overlapping pulse sets. Each replacement stimulation pulse is delivered within both timing channels. For example, as shown in FIG. 13, the IPG 14 selects the stimulation pulse in the pulsed electrical waveform 100*a* to replace the first potentially overlapping pulse set, then selects the stimulation pulse in the pulsed electrical waveform 100*b* to replace the second potentially overlapping pulse set, then selects the stimulation pulse in the pulsed electrical waveform 100*a* to replace the third potentially overlapping pulse set, etc. As shown in FIG. 14, each replacement stimulation pulse can be delivered within only the timing channel from which it was selected. Essentially, the stimulation pulse of the respective potentially overlapping pulse set that is not selected is suppressed, such that no stimulation pulse is delivered in the timing channel when the selected stimulation pulse is delivered in the other timing channel.

In yet another embodiment, the IPG 14 assigns one of the timing channels as a high priority timing channel, and selects the stimulation pulse associated with the high priority timing channel as the replacement stimulation pulse for a series of potentially overlapping pulse sets. If the timing channels are respectively associated with different tissue regions, the timing channel associated with the tissue region that would be more adversely affected by dropping a stimulation pulse within the timing channel can be assigned as the high priority timing channel (e.g., in response to a user input via the CP 18 or RC 16). Each replacement stimulation pulse is delivered within the high priority timing channel. Essentially, the stimulation pulse of the lower priority timing channel is suppressed. For example, as shown in FIG. 15, the IPG 14 assigns Timing Channel B as the high-priority channel, and selects the stimulation pulse of the pulsed electrical waveform 100*b* as the replacement stimulation pulse for all of the potentially overlapping pulse sets. As shown in FIG. 15, each replacement stimulation pulse is delivered only in Timing Channel B. Alternatively, each replacement stimulation pulse can be delivered in both Timing Channels A and B.

This embodiment may be especially useful when stimulating a key structure in the brain that requires highly regular pulsed frequencies, with the timing channel associated with the key structure having a high priority. Also, although this embodiment is discussed in the context of DBS, in occipital nerve stimulation, lesser occipital nerve stimulation may be a lower priority than greater occipital nerve stimulation. In this case, the timing channel associated with the greater occipital nerve stimulation will be given high priority, such that the stimulation pulse within the potentially overlapping pulse associated with greater occipital nerve stimulation will be selected as the replacement stimulation pulse.

Although the stimulation pulses in the potentially overlapping pulse sets have been described as being cathodic, it should be noted that the overlapping pulse sets can be anodic, in which case, the same techniques can be applied. If one pulse in a potentially overlapping pulse set is anodic and another pulse in the same potentially overlapping pulse set is cathodic, other techniques can be utilized to resolve this conflict. For example, as illustrated in FIG. 16, two timing channels (Channel A and Channel B) of the IPG 14 may be programmed by the CP 18 (or alternatively, the RC 16) with two pulsed electrical waveforms 100c, 100d, respectively, which when delivered by the IPG 14, will provide treatment to the patient in which the IPG 14 has been implanted.

As with the pulsed electrical waveforms 100a, 100b illustrated in FIG. 8, without modification, certain sets of respective pulses of the electrical waveforms 100c, 100d will temporally overlap each other (either partially or completely). Again, the IPG 14 may determine the sets of pulses that will potentially overlap each other temporally prior to their delivery within the respective timing channels, and replace each of these potentially overlapping pulse sets with a pulse, such that each pulse is delivered within at least one of the respective timing channels (and thus, delivered to the both electrode combinations assigned to the timing channels), thereby preventing temporal overlap between the pulses of the respective pulsed electrical waveforms 100c, 100d.

In this embodiment, however, the cathodic pulse in each potentially overlapping pulse set of the electrical waveforms 100c, 100d is selected as the replacement stimulation pulse, as illustrated in FIG. 17. Significantly, cathodic pulses are often the stimulating pulses, and are therefore, more important than anodic pulses, which are generally not stimulating. As such, retaining the cathodic pulse as the replacement stimulation pulse, while discarding or suppressing the anodic pulse, may not adversely affect therapy. In applications where the anodic pulses are used as the stimulating pulses, the anodic pulse may be retained as the replacement stimulation pulse, while the cathodic pulse is discarded or suppressed.

Instead of replacing each of the potentially overlapping pulse sets with a pulse in the manner discussed above with respect to FIGS. 9-17, the microcontroller 62 of the IPG 14 may temporally shift pulses in the respective pulsed electrical waveforms in a manner that prevents overlap of the determined pulse sets while preventing frequency locking between the timing channels.

In one embodiment, the IPG 14 alternately shifts stimulation pulses within the potentially overlapping pulse sets. For example, as shown in FIG. 18, the IPG 14 temporally shifts the stimulation pulse of the pulsed electrical waveform 100a for the first potentially overlapping pulse set, temporally shifts the stimulation pulse of the pulsed electrical waveform 100b for the second potentially overlapping pulse set, temporally shifts the stimulation pulse of the pulsed electrical waveform 100a for the third potentially overlapping pulse set, etc. Notably, the IPG 14 shifts each of the stimulation pulses in the direction that would minimize the amount that the stimulation pulses are shifted from their original position. For example, in FIG. 18, the stimulation pulse in the pulsed electrical waveform 100a is shifted forward in time for the first potentially overlapping pulse set, the stimulation pulse in the pulsed electrical waveform 100b is shifted backward in time for the second potentially overlapping pulse set, and the stimulation pulse in the pulsed electrical waveform 100a is shifted forward time for the third potentially overlapping pulse set.

In another embodiment, the IPG 14 temporally shifts one of the stimulation pulses of each potentially overlapping pulse set forward, and temporally shifts the other of the stimulation pulses of the each potentially overlapping pulse set backward. Notably, the IPG 14 shifts each of the stimulation pulses in the direction that would minimize the amount that the stimulation pulses are shifted from their original position. For example, as shown in FIG. 19, the stimulation pulse in the electrical waveform 100a is shifted backward in time, and the stimulation pulse in the electrical waveform 100b is shifted forward in time for the first potentially overlapping pulse set, the stimulation pulse in the electrical waveform 100a is shifted forward in time, and the stimulation pulse in the electrical waveform 100b is shifted backward in time for the second potentially overlapping pulse set, and the stimulation pulse in the electrical waveform 100a is shifted forward in time, and the stimulation pulse in the electrical waveform 100b is shifted backward in time for the third potentially overlapping pulse set In still another embodiment, the IPG 14 determines which stimulation pulse of each of the potentially overlapping pulse sets would need to be shifted the least to prevent overlapping of the stimulation pulses within the respective potentially overlapping pulse set, and temporally shifts that stimulation pulse within the timing channel.

Figure 20:
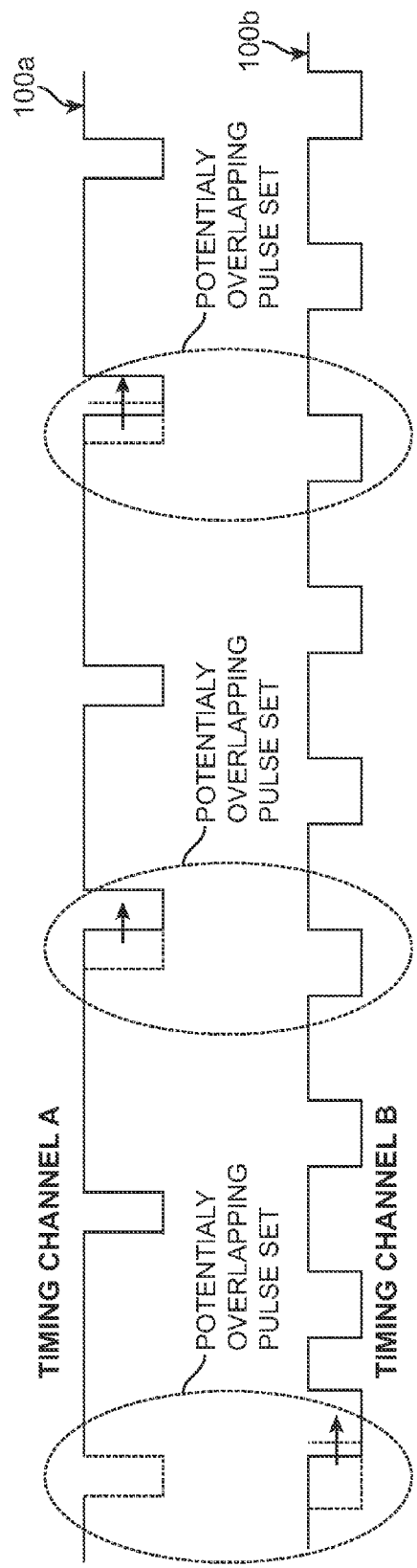
FIG. 20 is a timing diagram of two pulsed electrical waveforms delivered within two respective timing channels of the IPG of FIG. 3, wherein an eleventh technique is used to prevent temporal overlap between the pulses of the respective electrical waveforms.

For example, as shown in FIG. 20, for the second and third overlapping pulse sets, the stimulation pulses in the electrical waveform 100a would need to be shifted forward the least as compared to the stimulation pulses in the electrical waveform 100b, and thus, the stimulation pulses in the electrical waveform 100a are temporally shifted forward within the Timing Channel A. With respect to the first overlapping pulse set, the respective stimulation pulses of the electrical waveforms 100a, 100b would need to be shifted forward an equal amount to prevent the overlapping of the stimulation pulses. In this case, selection of the stimulation pulse that is to be temporally shifted can be performed arbitrarily or based on other criteria.

In the example illustrated in FIG. 20, the pulses in the electrical waveforms 100a and 100b are temporally shifted forward within the respective Timing Channels A and B. It should be appreciated that the pulses may be temporally shifted backward to avoid overlapping of the pulses. Selection of whether the pulses are to be shifted forward or backward may be determined based on any one of a variety of criteria. For example, the user or the system 10 may select the direction (either forward or backward) in which the pulses are to be shifted, or the direction in which the pulses are to be shifted may alternate or be randomly or pseudo-randomly selected. In these examples, the pulse that needs to be shifted the least in the selected direction would be shifted to prevent overlap.

In yet another embodiment, the IPG 14 predicts sets of stimulation pulses within the pulsed electrical waveforms that will not temporally overlap prior to their delivery within the respective timing channels, and temporally shifts at least one stimulation pulse in each of the potentially non-overlapping pulse sets. Thus, when the stimulation pulses are getting closer to the potentially overlapping pulse set (e.g., 4 pulses away), the IPG 14 may slightly shift one or both stimulation pulses of the pulsed electrical waveforms before they overlap. The advantage of this technique is that the stimulation pulses will only need to slightly be shifted in time from their original position, so that the frequency of the original pulsed electrical waveform is closer to the frequency of the modified pulsed electrical waveform.

Figure 21:
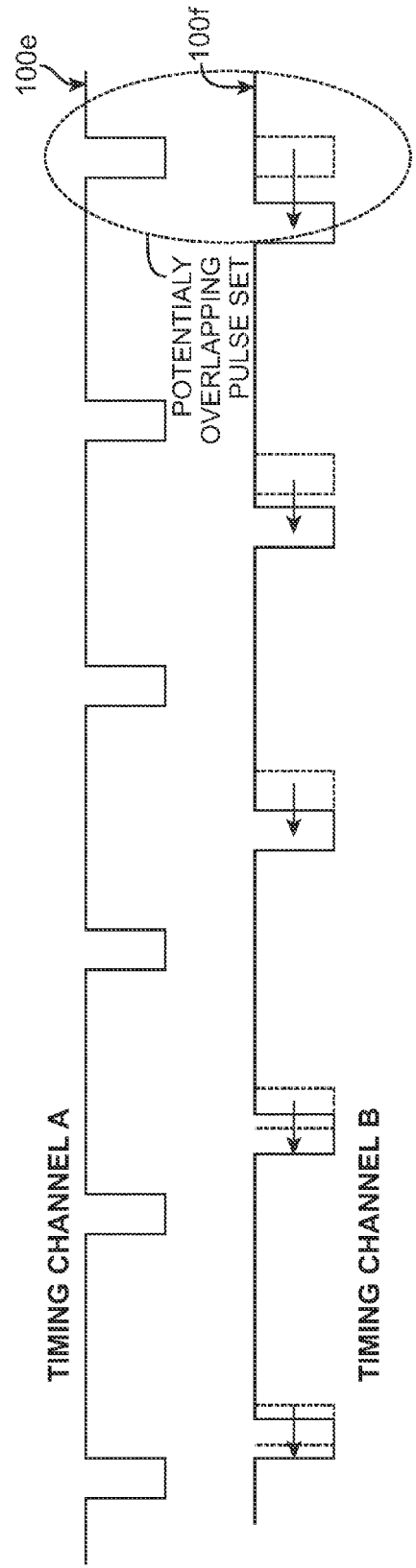
FIG. 21 is a timing diagram of two pulsed electrical waveforms delivered within two respective timing channels of the IPG of FIG. 3, wherein a twelfth technique is used to prevent temporal overlap between the pulses of the respective electrical waveforms.

For example, as shown in FIG. 21, two timing channels (Channel A and Channel B) of the IPG 14 may be programmed by the CP 18 (or alternatively, the RC 16) with two pulsed electrical waveforms 100*e*, 100*f*, respectively, which when delivered by the IPG 14, will provide treatment to the patient in which the IPG 14 has been implanted. As with the pulsed electrical waveforms 100*a*, 100*b* illustrated in FIG. 8, without modification, certain sets of respective stimulation pulses of the electrical waveforms 100*e*, 100*f* will temporally overlap each other (either partially or completely).

However, rather than shifting only one or both of the stimulation pulses in the potentially overlapping pulse set, the stimulation pulses of the potentially non-overlapping pulse sets previous to the potentially overlapping pulse set are temporally shifted to prevent the stimulation pulses from bunching up. In this case, the stimulation pulses of the potentially non-overlapping pulse sets are shifted slightly backward, so that when the stimulation pulse of the subsequent potentially overlapping pulse set is shifted backward to prevent overlap, the deviation of the spacings between the resulting stimulation pulses and the spacings between the original unshifted stimulation pulses will be slight. Essentially, the frequency of the resulting pulsed electrical waveforms will vary only slightly from the original frequency of the original pulsed electrical waveforms.

Although the stimulation pulses in the potentially non-overlapping pulse sets and potentially overlapping pulse sets are illustrated as being shifted forward time (essentially, decreasing the frequency of the electrical waveform), it should be appreciated that the stimulation pulses may be shifted backward in time (essentially, increasing the frequency of the electrical waveform).

Figure 22:
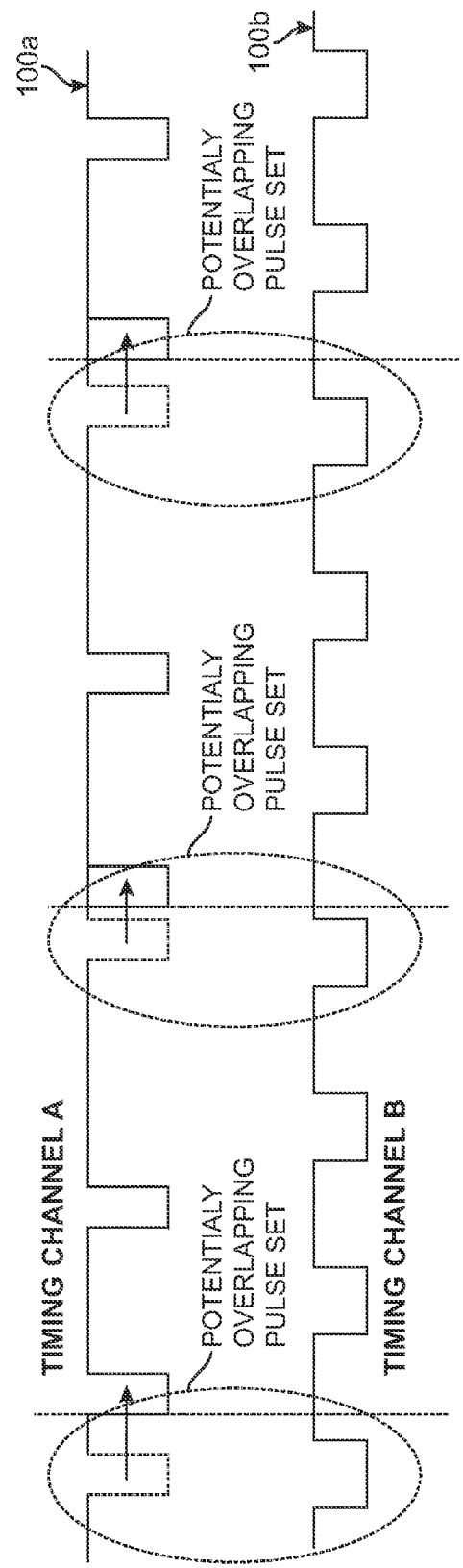
FIG. 22 is a timing diagram of two pulsed electrical waveforms delivered within two respective timing channels of the IPG of FIG. 3, wherein a thirteenth technique is used to prevent temporal overlap between the pulses of the respective electrical waveforms.

In yet another embodiment, the IPG 14 temporally shifts one or both of the stimulation pulses in the potentially overlapping pulse set by a randomized amount. For the purposes of this specification, a random value includes a pseudo-random value (i.e., a process that appears random, but is not, and exhibits statistical randomness while being generated by an entirely deterministic causal process). The value of the random amount can be computed using a conventional pseudo-random generator. The IPG 14 may determine the randomized amount of time that the stimulation pulse or pulses are shifted by multiplying a nominal pulse shift (e.g., the time shift used to prevent pulse overlap) with a randomization variable. In order to prevent ineffective treatment, the IPG 14 may limit the difference between the randomized amount and normal time shift (e.g., 16 msec). For example, as shown in FIG. 22, the stimulation pulses in the electrical waveform 100*a* are shifted forward a randomized amount of time. As shown by the dashed lines in each of the potentially overlapping pulse sets, the difference between the randomized shift and the nominal shift needed to prevent overlap between the respective pulses is different for each of the potentially overlapping pulse sets, indicating that that the pulses shifts are randomized.

It should be noted that the embodiments illustrated in FIGS. 18-22 do not shift the stimulation pulses of a particular electrical waveform that are subsequently delivered after a stimulation pulse that has been shifted within the same electrical waveform if the subsequent stimulation pulses do not temporally overlap the pulses of the other electrical waveform. That is, the stimulation pulses in each pulsed electrical waveform that do not overlap the stimulation pulses in the other pulsed electrical waveform or waveforms remain in their original position regardless of any shifting of other stimulation pulses. In this manner, the frequency ratio between the respective pulsed electrical waveforms remains substantially the same. Alternatively, however, stimulation pulses of a particular electrical waveform, even though they would not temporally overlap with any stimulation pulse of the other electrical waveform or waveforms, may be shifted in order to maintain a uniform spacing between the pulses of the electrical waveform as much as possible. For example, if a stimulation pulse of a particular electrical waveform is shifted forward in time, the next stimulation pulse may be shifted forward in time the same amount in order to maintain the nominal spacing between the respective stimulation pulses. In this manner, the frequency of each pulsed electrical waveform is maintained as uniformly as possible.

In the previous embodiments, the pulsed electrical waveforms are illustrated and describes as being monophasic in nature. It should be appreciated that the pulsed electrical waveforms may be multiphasic (e.g., biphasic) in nature. In this case, a charge recovery pulse (either passive or active) will accompany each stimulation pulse, as illustrated in FIGS. 5*a* and 5*b*. In this case, the IPG 14 attempts to prevent the overlap between a charge recovery pulse delivered within one timing channel and a stimulation pulse delivered within another timing channel. For example, the IPG 14 may predict a charge recovery pulse and a stimulation pulse within the pulsed electrical waveforms that will potentially overlap temporally, and dropping or temporally shifting at least a portion of the charge recovery pulse, thereby preventing temporal overlap between the charge recovery pulse and the stimulation pulse of the respective electrical waveforms. In another embodiment, the IPG 14 drops or temporally shifts any charge recovery pulse associated with a stimulation pulse that is averaged or summed within another stimulation pulse (e.g., shown in FIGS. 11 and 12).

If a charge recovery phase is dropped or temporally shifted, the IPG 14 may employ an interlock algorithm to make sure that there is charge recovery after a certain number of drops or delays of the charge recovery pulse, a certain number of stimulation pulses, the next stimulation pulse, a set amount of time, an amount of time determined by a certain number of stimulation pulses, and/or a specified amount of charge is injected into the tissue (or before a specified amount is injected). If a charge recovery pulse is interrupted, a countdown time may be used to manage the length of the interrupted charge recovery pulse and make sure the remainder of the charge recovery pulse is completed.

The limit on the time between passive charge recovery pulses may also be determined by the amplitude, pulse width, and frequency of the pulses. For example, pulsed electrical waveforms with a high amplitude and short pulse width may require passive charge recovery pulses less often. Alternatively, coupling capacity may be measured at the end of each stimulation pulse to determine how much charge is injected into the tissue, and trigger the recharge pulse at the appropriate time and with the appropriate duration. Measurement of the coupling capacity may be accomplished by measuring the output bias on the output capacitors.

If a passive charge recovery pulse delivered in one timing channel temporally overlaps an active charge recovery pulse in another timing channel, the first charge recovery pulse in time may be interrupted to prevent overlap with the second charge recovery pulse in time.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for treating a patient using a multi-channel neurostimulation system, the method comprising:
delivering a plurality of pulsed electrical waveforms respectively within a plurality of timing channels of the neurostimulation system, thereby treating the patient;
predicting sets of stimulation pulses within the pulsed electrical waveforms that will potentially overlap temporally; and
temporally shifting stimulation pulses in the respective pulsed electrical waveforms in a manner that prevents overlap of the potentially overlapping pulse sets while preventing frequency locking between the timing channels, wherein temporally shifting stimulation pulses in the respective pulsed electrical waveforms comprises alternately shifting one of the stimulation pulses of each potentially overlapping pulse set between the timing channels.

2. A method for treating a patient using a multi-channel neurostimulation system, the method comprising:
delivering a plurality of pulsed electrical waveforms respectively within a plurality of timing channels of the neurostimulation system, thereby treating the patient;
predicting sets of stimulation pulses within the pulsed electrical waveforms that will potentially overlap temporally; and
temporally shifting stimulation pulses in the respective pulsed electrical waveforms in a manner that prevents overlap of the potentially overlapping pulse sets while preventing frequency locking between the timing channels, wherein temporally shifting stimulation pulses in the respective pulsed electrical waveforms comprises:
temporally shifting one of the stimulation pulses of each potentially overlapping pulse set forward; and
temporally shifting another of the stimulation pulses of each potentially overlapping pulse set backward.

3. A method for treating a patient using a multi-channel neurostimulation system, the method comprising:
delivering a plurality of pulsed electrical waveforms respectively within a plurality of timing channels of the neurostimulation system, thereby treating the patient;
predicting sets of stimulation pulses within the pulsed electrical waveforms that will potentially overlap temporally; and
temporally shifting stimulation pulses in the respective pulsed electrical waveforms in a manner that prevents overlap of the potentially overlapping pulse sets while preventing frequency locking between the timing channels, wherein temporally shifting stimulation pulses in the respective pulsed electrical waveforms comprises:
determining which pulse of each potentially overlapping pulse set would need to be shifted the least to prevent overlapping of the stimulation pulses within the respective potentially overlapping pulse set; and
temporally shifting the determined pulse of each potentially overlapping pulse set.

4. A method for treating a patient using a multi-channel neurostimulation system, the method comprising:
delivering a plurality of pulsed electrical waveforms respectively within a plurality of timing channels of the neurostimulation system, thereby treating the patient;
predicting sets of stimulation pulses within the pulsed electrical waveforms that will potentially overlap temporally; and
temporally shifting stimulation pulses in the respective pulsed electrical waveforms in a manner that prevents overlap of the potentially overlapping pulse sets while preventing frequency locking between the timing channels, wherein temporally shifting stimulation pulses in the respective pulsed electrical waveforms comprises:
determining sets of stimulation pulses within the pulsed electrical waveforms that will not potentially overlap temporally; and
temporally shifting at least one pulse in each of the non-overlapping pulse sets.

5. A method for treating a patient using a multi-channel neurostimulation system, the method comprising:
delivering a plurality of pulsed electrical waveforms respectively within a plurality of timing channels of the neurostimulation system, thereby treating the patient;
predicting sets of stimulation pulses within the pulsed electrical waveforms that will potentially overlap temporally; and
temporally shifting stimulation pulses in the respective pulsed electrical waveforms in a manner that prevents overlap of the potentially overlapping pulse sets while preventing frequency locking between the timing channels, wherein temporally shifting stimulation pulses in the respective pulsed electrical waveforms comprises temporally shifting at least one pulse in each potentially overlapping pulse set a random amount.

6. The method of claim 5, further comprising determining the random amount by multiplying a nominal pulse shift by a randomization variable.

7. The method of claim 6, further comprising limiting the random amount that differs from the nominal pulse shift.

8. A multi-channel neurostimulation system, comprising:
a plurality of electrical terminals configured for being respectively coupled to a plurality of electrodes;
analog output circuitry configured for delivering a plurality of pulsed electrical waveforms respectively within a plurality of timing channels to the electrical terminals; and
control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels, wherein the control circuitry is configured for shifting stimulation pulses in the respective pulsed electrical waveforms by alternately shifting one of the stimulation pulses of each potentially overlapping pulse set between the timing channels.

9. A multi-channel neurostimulation system, comprising:
a plurality of electrical terminals configured for being respectively coupled to a plurality of electrodes;
analog output circuitry configured for delivering a plurality of pulsed electrical waveforms respectively within a plurality of timing channels to the electrical terminals; and
control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels, wherein the control circuitry is configured for temporally shifting stimulation pulses in the respective pulsed electrical by temporally shifting one of the stimulation pulses of each potentially overlapping pulse set forward, and temporally shifting another of the stimulation pulses of each potentially overlapping pulse set backward.

10. A multi-channel neurostimulation system, comprising:
a plurality of electrical terminals configured for being respectively coupled to a plurality of electrodes;
analog output circuitry configured for delivering a plurality of pulsed electrical waveforms respectively within a plurality of timing channels to the electrical terminals; and
control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels, wherein the control circuitry is configured for temporally shifting stimulation pulses in the respective pulsed electrical waveforms by determining which pulse of each potentially overlapping pulse set would need to be shifted the least to prevent overlapping of the stimulation pulses within the respective potentially overlapping pulse set, and temporally shifting the determined pulse of each potentially overlapping pulse set.

11. A multi-channel neurostimulation system, comprising:
a plurality of electrical terminals configured for being respectively coupled to a plurality of electrodes;
analog output circuitry configured for delivering a plurality of pulsed electrical waveforms respectively within a plurality of timing channels to the electrical terminals; and
control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels, wherein the control circuitry is configured for temporally shifting stimulation pulses in the respective pulsed electrical waveforms by determining sets of stimulation pulses within the pulsed electrical waveforms that will not potentially overlap temporally, and temporally shifting at least one pulse in each of the non-overlapping pulse sets.

12. A multi-channel neurostimulation system, comprising:
a plurality of electrical terminals configured for being respectively coupled to a plurality of electrodes;
analog output circuitry configured for delivering a plurality of pulsed electrical waveforms respectively within a plurality of timing channels to the electrical terminals; and
control circuitry configured for predicting sets of stimulation pulses within the pulsed electrical waveforms that will potentially overlap temporally, and temporally shifting stimulation pulses in the respective pulsed electrical waveforms in a manner that prevents overlap of the potentially overlapping pulse sets while preventing frequency locking between the timing channels, wherein the control circuitry is configured for temporally shifting stimulation pulses in the respective pulsed electrical waveforms by temporally shifting at least one pulse in each potentially overlapping pulse set a random amount.

13. The neurostimulation system of claim 12, wherein the control circuitry is configured for determining the random amount by multiplying a nominal pulse shift by a randomization variable.

14. The neurostimulation system of claim 12, wherein the control circuitry is further configured for limiting the random amount that differs from the nominal pulse shift.

* * * * *